US010658068B2

(12) United States Patent
Delaney et al.

(10) Patent No.: US 10,658,068 B2
(45) Date of Patent: *May 19, 2020

(54) EVOLUTIONARY MODELS OF MULTIPLE SEQUENCE ALIGNMENTS TO PREDICT OFFSPRING FITNESS PRIOR TO CONCEPTION

(71) Applicant: Ancestry.com DNA, LLC, Lehi, UT (US)

(72) Inventors: Nigel Delaney, San Francisco, CA (US); Ari Silver, New York, NY (US); Lee Silver, New York, NY (US)

(73) Assignee: Ancestry.com DNA, LLC, Lehi, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/568,456

(22) Filed: Dec. 12, 2014

(65) Prior Publication Data

US 2015/0363546 A1 Dec. 17, 2015

Related U.S. Application Data

(60) Provisional application No. 62/013,139, filed on Jun. 17, 2014.

(51) Int. Cl.
*G16B 20/00* (2019.01)
*G16B 5/00* (2019.01)
*G16B 10/00* (2019.01)

(52) U.S. Cl.
CPC .............. *G16B 20/00* (2019.02); *G16B 5/00* (2019.02); *G16B 10/00* (2019.02)

(58) Field of Classification Search
None
See application file for complete search history.

(56) References Cited

U.S. PATENT DOCUMENTS

| | | | |
|---|---|---|---|
| 8,620,594 B2 | 12/2013 | Silver | |
| 8,805,620 B2 | 8/2014 | Silver | |
| 2004/0030503 A1 | 2/2004 | Arouh et al. | |
| 2006/0111849 A1 | 5/2006 | Schadt et al. | |
| 2012/0310539 A1 | 12/2012 | Crockett et al. | |
| 2014/0304270 A1 | 10/2014 | Torkamani | |
| 2015/0066378 A1 | 3/2015 | Robison et al. | |

FOREIGN PATENT DOCUMENTS

| | | |
|---|---|---|
| WO | WO 2011/038155 | 3/2011 |
| WO | WO 2011/050076 | 4/2011 |
| WO | WO 2014/089356 | 6/2014 |
| WO | WO-2015/042496 A1 | 3/2015 |

OTHER PUBLICATIONS

Primmer, C.R. et al., Prediction of offspring fitness based on parental genetic diversity in endangered salmonid populations, Journal of Fish Biology, 2003, 909-927, 63.

Cooper, Gregory M., Distribution and intensity of constraint in mammalian genomic sequence, Apr. 20, 2005, p. 901-913, 15, Genome Research.

Kingsmore, Stephen, Comprehensive Carrier Screening and Molecular Diagnostic Testing for Recessive Childhood Diseases, May 2, 2012. www.ncbi.nlm.nih.gov/pmc/articles/PMC3392137/?report=printable.

Choi Y, Sims GE, Murphy S, Miller JR, Chan AP (2012) Predicting the Functional Effect of Amino Acid Substitutions and Indels. PLoS ONE 7(10): e46688.

Office Action issued by the United States Patent and Trademark Office for U.S. Appl. No. 14/886,520 dated Jan. 20, 2016.

Baskovich et al. "Expanded genetic screening panel for the Ashkenazi Jewish population", Genetics in Medicine, 2016, vol. 18, No. 5, pp. 522-528.

Li, et al., "Generating Samples for Association Studies Based on HapMap Data", BioMed Central, BMC Bioinformatics, Jan. 24, 2008, vol. 9, No. 44, pp. 1-13.

Silver et al. "Carrier Screening is a Deficient Strategy for Determining Sperm Donor Eligibility and Reducing Risk of Disease in Recipient Children", Genetic Testing and Molecular Biomarkers, 2016, vol. 20, No. 6, pp. 276-284.

Srinivasan et al. "A universal carrier test for the long tail of Mendelian disease", Reproductive BioMedicine Online, 2010, pp. 537-551.

Burke et al. "Genetic Screening", Epidemiologic Reviews, Jun. 27, 2011, vol. 33, pp. 148-164.

Callum et al. "Spinal muscular atrophy (SMA) after conception using gametes from anonymous donors: recommendations for the future", Fertility and Sterility, Feb. 2010, vol. 93, No. 93, pp. 1006.e1-1006.e2.

Eypasch et al. "Probability of adverse events that have not yet occurred: a statistical reminder", Fertility and Sterility, Sep. 2, 1995, vol. 311, No. 93, pp. 619-620.

Green et al. "Psychosocial aspects of genetic screening of pregnant women and newborns: a systematic review", Health Technology Assessment, 2004, vol. 8, No. 33, pp. 1-4.

Levenson, "Genetic discrimination lawsuit raises broader concerns about testing, privacy", American Journal of Medical Genetics, 2016, pp. 1111-1112.

(Continued)

*Primary Examiner* — Joseph Woitach
(74) *Attorney, Agent, or Firm* — Fenwick & West LLP

(57) ABSTRACT

A system, device and method for receiving multiple aligned genetic sequences obtained from genetic samples of multiple organisms of one or more different species. A measure of evolutionary variation may be computed for one or more alleles at each of one or more aligned genetic loci. The aligned genetic loci in the multiple organisms may be derived from one or more common ancestral genetic loci or may be otherwise related. The measure of evolutionary variation may be a function of variation in alleles at corresponding aligned genetic loci in the multiple aligned genetic sequences. One or more likelihoods may be computed that an allele mutation at each of the one or more genetic loci in a simulated virtual progeny will be deleterious based on the measure of evolutionary variation of alleles at the corresponding aligned genetic loci for the multiple organisms.

23 Claims, 5 Drawing Sheets

(56) References Cited

OTHER PUBLICATIONS

Martin et al. "Comprehensive carrier genetic test using next-generation deoxyribonucleic acid sequencing in infertile couples wishing to conceive through assisted reproductive technology", Fertility and Sterility, Nov. 2015, vol. 104, No. 5, pp. 1286-1293.
Larson et al., "Validation of a high resolution NGS method for detecting spinal muscular atrophy carriers among phase 3 participants in the 1000 Genomes Project", BMC Medical Genetics, (2015), 16:100, pp. 1-14.
Picard Tools, Broad Institute, https://broadinstitute.github.io/picard/ ; printed on Mar. 14, 2017.
SAMtools, GitHub Social Coding http://samtools.sourceforge.net/ , Last Modified: Sep. 12, 2012.
Wiki, Snakemake/Documentation http://snakemake.readthedocs.io/en/stable/ ; 2014-2016.
View Run & Lane Metrics, Illumina, BaseSpace Online Help https://support.illumina.com/help/BaseSpace_OLH_009008/Content/Vault/Informatics/Sequencing_Analysis/BS/swSEQ_mBS_ViewRunSamplesList.htm; printed on Mar. 14, 2017.
The Variant Call Format (VCF) Version 4.2 Specification, Nov. 15, 2016, https://github.com/samtools/hts-specs, pp. 1-28.
GenePeeks, Inc., GitHub, Inc. [US], https://github.com/GenePeeks; printed on Mar. 14, 2017.
Data Protection, Amazon Web Services, https://aws.amazon.com/s3/faqs/#data-protection; printed on Mar. 14, 2017.
Burrows—Wheeler Aligner http://bio-bwa.sourceforge.net/, Last Modified: Feb. 28, 2010.
Amazon EC2 Instance Types, Amazon Web Services https://aws.amazon.com/ec2/instance-types/; printed on Mar. 14, 2017.
Reads-to-variants workflows used at the Broad Institute, GATK Best Practices, Recommended workflows for variant discovery analysis with GATK, GATK https://software.broadinstitute.org/gatk/best-practices/; printed on Mar. 14, 2017.
GregoryFaust/samblaster, GitHub, Inc. [US] https://github.com/GregoryFaust/samblaster, Published on May 7, 2014.
HaplotypeCaller, Call germline SNPs and indels via local re-assembly of haplotypes, GATK https://software.broadinstitute.org/gatk/documentation/tooldocs/current/org_broadinstitute_gatk_tools_walkers_haplotypecalier_haplotypecaller.php; Feb. 9, 2017.
Resource at: https://support.illumina.com/content/dam/illumina-support/documents/downloads/software/bcl2fastq/bcl2fastq2-v2-18-software-guide-15051736-01.pdf; Apr. 2016.
BaseRecalibrator, Detect systematic errors in base quality scores, GATK Best Practices, GATK, https://software.broadinstitute.org/gatk/documentation.tooldocs/current/org_broadinstitute_gatk_tools_walkers_bosr_BaseRecalibrator.php; Jul. 29, 2017.
MongoDB Documentation https://docs.mongodb.com/?_ga=1.52591085.459598860.1467921146; Jul. 26, 2017.
HaplotypeCaller https://software.broadinstitute.org/gatk/documentation/tooldocs/current/org_broadinstitute_gatk_tools_walkers_haplotypecaller_HaplotypeCaller.php; Jul. 29, 2017.
Genome Profile DataBase http://godb.life.nthu.edu.tw/GPDB/index.php ; 2006.
PCT International Search Report and Written Opinion, PCT Application No. PCT/US15/36016, dated Sep. 21, 2015, 16 pages.
PCT International Search Report and Written Opinion, PCT Application No. PCT/US16/28818, dated Sep. 27, 2016, 23 pages.
Quang, D. et al., "DANN: a deep learning approach for annotating the pathogenicity of genetic variants," Bioinformatics, 2014, vol. 31, No. 5, pp. 761-763.
Bromberg, Y. et al., "SNAP: predict effect of non-synonymous polymorphisms on function," Nucleic acids research, 2007, vol. 35, No. 11, pp. 3823-3835.
Ferrer-Costa, C. et al., "PMUT: a web-based tool for the annotation of pathological mutations on proteins," Bioinformatics, 2005, vol. 21, No. 14, pp. 3176-3178.

Fig. 1

EVOLUTIONARY MODELS OF MULTIPLE SEQUENCE ALIGNMENTS TO PREDICT OFFSPRING FITNESS PRIOR TO CONCEPTION

REFERENCE TO RELATED APPLICATIONS

This patent application claims benefit of U.S. provisional patent application Ser. No. 62/013,139 filed Jun. 17, 2014, which is incorporated herein by reference in its entirety.

FIELD OF THE INVENTION

Embodiments of the invention relate to predictions of evolutionary fitness of genes in a population of organisms. In particular, some embodiments of the invention relate to the use of genetic variation, whether within a single species or across multiple species, to predict the fitness of hypothetical or virtual offspring associated with a potential mating before that mating occurs.

BACKGROUND OF THE INVENTION

Every year thousands of babies are born with genetic diseases. Often, the parents of these children are both healthy, but each parent possesses genetic mutations that when passed in combination to the child, endow it from the time of conception with an unmitigated genetic defect. Children with such diseases may suffer, have diminished lifespans and can entail large emotional and financial costs, so many prospective parents attempt to minimize the chance that they pass on genetic elements that cause disease.

Carrier testing, in which both parents are genotyped at loci of their genomes that are known to cause disease, is a technique widely used to achieve this goal. Such tests rely on a defined set of alleles known to cause diseases, and then screen for the presence of these alleles in one or both parents prior to conception. The alleles screened in such tests typically have been established to cause disease by examining pedigrees of patients with the disease, by using cellular or animal models of the effect of the particular allele, or alternate means. In all cases, the correlation between alleles and genetic diseases are determined by studying one or more individuals that have already been born.

Although carrier testing is used in a limited number of cases, even if all possible prospective matings were filtered by this technique, children suffering from genetic diseases would still be born. This is because carrier tests inherently screen only a known subset of all alleles that can cause disease. The incompleteness of these tests is evidenced by the fact that the number of alleles associated with disease in public databases such as ClinVar (http://www.ncbi.nlm.nih.gov/clinvar/) and OMIM (http://www.ncbi.nlm.nih.gov/omim) continues to grow every year, and in turn so do the number of loci tested by carrier screening. Similarly, many patients can present with pathologies which appear to have a genetic basis, but for which no specific underlying genetic mutation has yet been determined. In many of these cases, a novel pathogenic variant or variants is then later discovered by various means and added to the catalog of known disease associated mutations. For example, the genomes of many patients with similar pathologies can be sequenced and shared mutations found. Alternatively, mutations that occur in an individual patient's genome which appear damaging (missense, nonsense, etc.) and are present in genes known to be associated with a biological process related to the pathology, may be tested in a cellular or animal model.

While the steady increase of the catalog of variants known to cause disease implies that carrier testing will get better, it also evinces that it suffers from two fundamental inadequacies. The first is that a diseased child must be born and diagnosed in order to find a new disease associated allele. The second, and more insidious, is that carrier testing cannot assess the impact of novel or de novo mutations. If a variant is specific to an individual or family and has not been previously studied, carrier testing cannot determine what effect it may have on future offspring. Additionally, because novel variants initially only appear as one half of a heterozygote genotype, if the allele is recessive, but damaging when combined with itself or another recessive mutation, it is very difficult to resolve the effect of the mutation until, from the perspective of a parent who wants to avoid passing on disease causing alleles, it is too late.

SUMMARY OF THE INVENTION

A system, device and method are described to overcome the aforementioned issues in the art. Some embodiments may assign one or more likelihoods that an allele mutation in a simulated virtual progeny is deleterious based on the evolutionary variation at the allele loci in real extant species or populations, for example, in order to filter out prospective pairings of gametes prior to conception.

According to some embodiments of the invention, a system, device and method may use the evolution of genetic variation of multiple organisms within one species ("single-species" or "intra-species" model) or across multiple different species ("multi-species" or "inter-species" model) to predict the likelihood that alleles would be deleterious in hypothetical, simulated or virtual progeny. Past evolutionary trends in allele mutations of extant or surviving (currently or once-living) organisms representative of one or more species or populations may be analyzed to predict the future fitness of a potential hypothetical or virtual (never or non-living) progeny simulated for two potential parents.

According to some embodiments of the invention, a system, device and method may receive multiple aligned genetic sequences obtained from genetic samples of multiple organisms of one or more different species. Genetic loci are aligned from different sequences for different organisms that are derived from one or more common ancestral genetic loci correlated with the same trait(s), disease(s), codon(s), that are positioned or sandwiched between other correlated marker loci, or that are otherwise related. A measure of evolutionary variation may be computed for one or more alleles at each of one or more aligned genetic loci of the multiple aligned sequences. The measure of evolutionary variation may be a function of variation in alleles at corresponding aligned genetic loci in the multiple aligned genetic sequences. One or more likelihoods may be computed that an allele, either a new mutation or one present in the alignment, at each of the one or more genetic loci in a simulated virtual progeny will be deleterious based on the measure of evolutionary variation of alleles at the corresponding aligned genetic loci for the multiple organisms.

According to some embodiments of the invention, a system, device and method may generate the virtual (hypothetical, potential or non-living) progeny by simulating a mating between two (living) potential parents by combining at least a portion of their genetic information. Simulating a mating may include combining genetic information of both of the two potential parents at one or more genetic loci. In one embodiment, a mating may be simulated by generating a virtual gamete for each potential parent by at least partially randomly selecting one of two allele copies in the parent's two sets of chromosomes to simulate recombination at each of one or more genetic loci. Two virtual gametes from the two respective potential parents may be combined to generate a genetic sequence of a virtual progeny.

Once the virtual progeny is simulated, alleles or mutations in the virtual progeny may be assigned the one or more of the likelihoods or scores determined for corresponding alleles or mutations in aligned loci of the multiple extant organisms. These likelihoods may indicate the potential or probability that the virtual progeny's alleles or mutations would be deleterious, for example, if those alleles or mutations were found in the genome of a living organism such as a human child.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1 schematically illustrates an example of an alignment of multiple genetic sequences (SEQ ID Nos.: 1-36, respectively, in order of appearance) according to an embodiment of the invention (the abbreviations for the species are as follows: LATCH=*Latimeria chalumnae*; XENTR=*Xenopus tropicalis*; TAEGU=*Taeniopygia guttata*; MELGA=*Meleagris gallopavo*; CHICK=*Gallus gallus*; ORNAN=*Ornithorhynchus anatinus*; LOXAF=*Loxodonta africana*; HORSE=*Equus caballus*; TURTR=*Tursiops truncatus*; MYOLU=*Myotis lucifugus*; AILME=*Ailuropoda melanoleuca*; OTOGA=*Otolemur gamettii*; CALJA=*Callithrix jacchus*; MACMU=*Macaca mulatta*; NOMLE=*Nomascus leucogenys*; PONAB=*Pongo abelii*; GORILLA=*Gorilla gorilla*; CHIMP=*Pan troglodytes*; HUMAN=*Homo sapiens*; TUPBE=*Tupaia belangeri*; OCHPR=*Ochotona princeps*; CAVPO=*Cavia porcellus*; SPETR=*Spermophilus tridecemlineatus*; DIPOR=*Dipodomys ordii*; MOUSE=*Mus musculus*; RAT=*Rattus norvegicus*; SARHA=*Sarcophilus harrisii*; MONDO=*Monodelphis domestica*; MACEU=*Macropus eugenii*; DANRE=*Danio rerio*; GADMO=*Gadus morhua*; ORYLA=*Oryzias latipes*; GASAC=*Gasterosteus aculeatus*; ORENI=*Oreochromis niloticus*; TETNG=*Tetraodon nigroviridis*; TAKRU=*Takifugu rubripes*);

Figure 2:
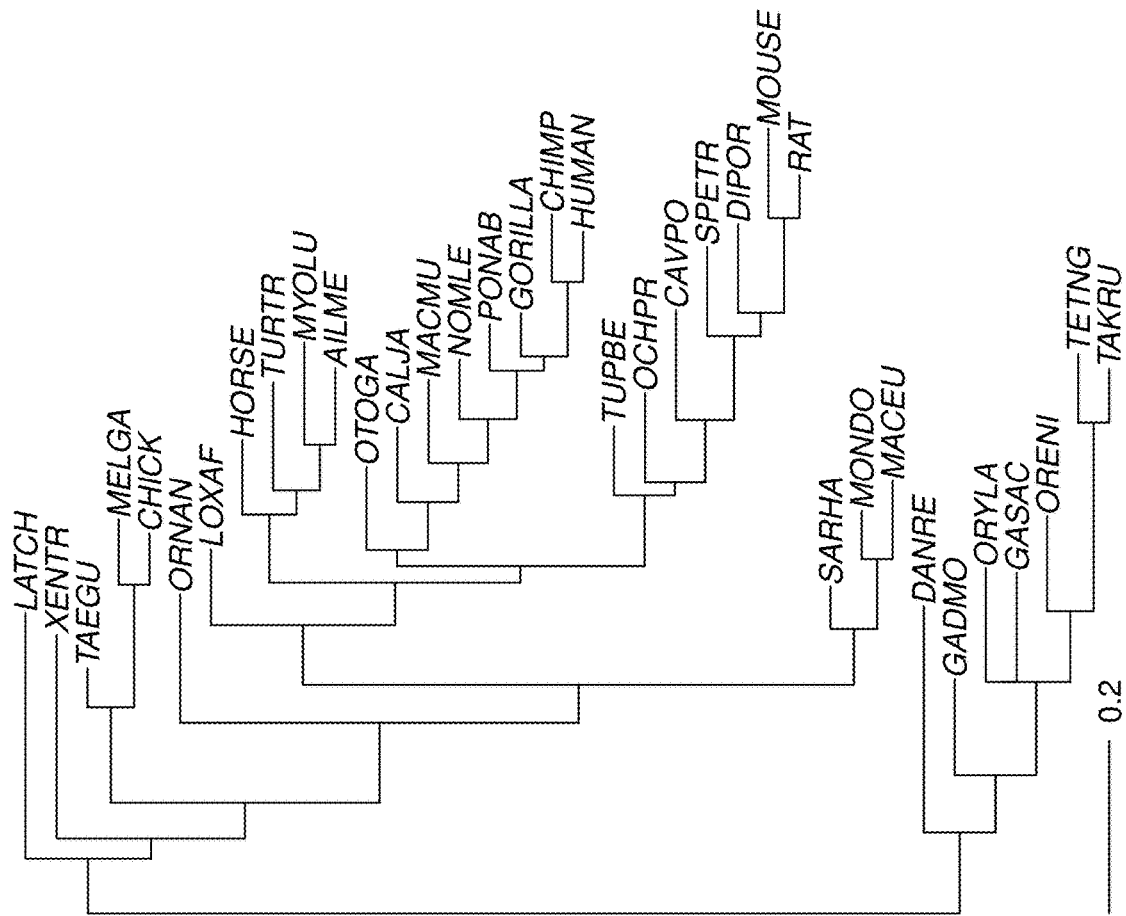
FIG. 2 schematically illustrates an example of a phylogenetic tree inferred from the multiple sequence alignment shown in FIG. 1 according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Embodiments of the invention relate to multiple types of genetic sequences:

Reference genetic sequences: Genetic sequences used to generate an evolutionary model, such as, a phylogenetic tree. Reference genetic sequences may include standardized genetic sequences from organisms representative of one or more evolutionarily extant (currently or previously living) populations or species, such as those released by genome consortia (e.g., human reference genome, such as, Genome Reference Consortium Human Build 37 (GRCh37) provided by the Genome Reference Consortium). Reference genetic sequences may additionally or alternatively include non-standardized sequences of organisms, such as, any member of a population or species. A single-species model may be generated using reference genetic sequences from multiple organisms of the same single species, e.g., 1,000 chimpanzee or humans. A multi-species model may be generated using reference genetic sequences from multiple organisms of multiple different species, e.g., one model using 1,000 humans, 10 chimpanzee and one gorilla, or another model using a single different organism from each different species as shown in FIG. 1. Reference genetic sequences may be used to analyze the evolution of successful (positive) or neutral (non-deleterious) allele mutations or variations across one or more extant species. An evolutionary model may predict likelihoods that allele mutations or variations would be deleterious based on their frequency or rarity of occurrence across the multiple reference genetic sequences. For example, allele mutations or variations that are relatively more rare across the reference genetic sequences may be considered negatively selected for evolutionarily (e.g. associated with a deleterious trait for which an organism cannot or has a relatively lower likelihood of surviving or reproducing), while allele mutations or variations that are relatively more common across the reference genetic sequences may be considered positively or neutrally selected for evolutionarily (e.g. not associated with a deleterious trait, but traits for which an organism has a neutral or improved likelihood of surviving or reproducing).

Potential parent genetic sequences: Genetic sequences of real (currently or previously living) potential parents, for example, from which genetic information is combined to simulate a virtual mating generating one or more virtual children or progeny, to predict before they conceive a child, a likelihood that such a child would have a deleterious trait. The potential parent genetic sequences may be obtained from genetic samples of two potential parents seeking to mate, or from a first potential parent seeking a genetic donor and a second potential parent from a pool of candidate donors.

Virtual progeny genetic sequences: Genetic sequences of simulated (never living) virtual progeny generated by simulating a mating or combining genetic information from two potential parent genetic sequences. Each virtual progeny genetic sequence may be a prediction or simulation of one possible genetic sequence of a child of the two potential parents, before that child is conceived. To achieve more robust results, the simulated mating may be repeated to generate multiple virtual progeny genetic sequences for each pair of potential parents. The virtual progeny genetic sequences may be compared to the reference genetic sequences, for example, to identify evolutionarily rare, and therefore, likely deleterious traits.

In some embodiments, genetic information may be used interchangeably for potential parent genetic sequences and reference genetic sequences. In one example, genetic information from a potential parent or donor may be used instead of, or in combination with reference consortium genetic sequences, to generate an evolutionary model or phylogenetic tree. In another example, reference consortium genetic sequences may be used instead of, or in combination with potential parent or donor genetic sequences, to simulate matings or predict likelihoods of deleterious traits in offspring.

As used herein, a "genetic sequence" may include genetic information representing one or more bases, nucleotides or alleles (sequences of nucleotides defining different forms of a gene) for any number of sequential or non-sequential genetic loci. For example, a "genetic sequence" may refer to allele information at a single genetic locus, or multiple genetic loci, such as, one or more gene segments or an entire genome. A genetic sequence is a data structure representing genetic information at one or more loci of a real or virtual genome. Genetic sequence data structures may include, for example, one or more vectors, scalar values, functions, sequences, sets, matrices, tables, lists, arrays, and/or other data structures, representing one or more bases, nucleotides, genes, alleles, codons or other generic material. The data structures representing each single chromosome sequence may be one dimensional (e.g., representing a single base or allele per locus) or multi-dimensional (e.g., representing multiple or all bases A, T, C, G or alleles at each locus and a probability associated with the likelihood of each existing in a potential progeny). The same (or different) data structures may be used for real and virtual genome sequences, though real genome sequences generally represent real genetic material (e.g., DNA extracted from a currently or previously existing genetic sample), while virtual genome sequences have no real corresponding genetic material (e.g., the sequence may represent an imaginary non-existing gamete, progeny, etc.).

According to some embodiments of the invention, multiple reference genetic sequences from multiple extant organisms within one species ("single-species" model) or multiple different species ("multi-species" model) may be used to generate an evolutionary model to predict deleterious allele mutations in virtual progeny. In one example of a multi-species model, multiple different vertebrate species may be used to predict deleterious allele mutations in virtual human progeny.

The reference genetic sequences may be aligned to link or associate one or more genetic loci in each of the multiple different sequences. Aligned loci of the different sequences may be derived from one or more common ancestral genetic loci and/or may relate to the same features, diseases or traits. A measure of evolutionary variation of alleles at one or more of the aligned genetic loci may be computed, for example, as a function of variation in alleles at corresponding aligned genetic loci in the multiple aligned reference genetic sequences. Aligned genetic loci associated with a relatively lower frequency of allele variation may indicate that the alleles are "functional" or relatively important to an organism's survival and their mutations may have a relatively higher likelihood of causing deleterious traits in an organism, whereas aligned genetic loci associated with a relatively higher frequency of allele variation in the reference genetic sequences may indicate that the alleles are less or non-functional and may be mutated with a relatively lower likelihood of impacting the survival or formation of deleterious traits in an organism. In some embodiments, the reference genetic sequences in the model may be weighted according to their evolutionary proximity of its population or species to the population or species of the virtual progeny and potential parent. For example, more weight may be assigned to reference genetic sequences of populations or species that are relatively more evolutionarily related (e.g., closer on a phylogenetic tree or having a relatively smaller Hamming distance).

Genetic sequences may be obtained from two potential parents, such as, two individuals that plan on mating or between one individual seeking a genetic donor and each of a plurality of candidates from a pool of genetic donors. The potential parents' genetic sequences may be obtained from genetic samples of biological material from the potential parents. A mating may be simulated between two potential parents, for example, by combining the genetic information from the two potential parents' genetic sequences to generate one or more genetic sequences of simulated virtual progeny.

The virtual progeny genetic sequences may be aligned with one or more of the reference genetic sequences to identify one or more alleles that evolved from the same ancestral genetic loci. The virtual progeny may be assigned one or more of the likelihoods of exhibiting deleterious traits associated with one or more alleles or mutations in the virtual progeny genetic sequences based on the measure of evolutionary variation of alleles at the corresponding aligned genetic loci in the reference genetic sequences.

Predicting Deleterious Alleles

Embodiments of the invention overcome the limitations of relying on specific information derived from human or cellular studies of the effect of mutation in order to score the propensity or probability that a particular mutation or allele will cause a deleterious phenotype, trait or disease.

An insight recognized according to embodiments of the invention is that extant genetic variation, that is existing or surviving genetic variation present amongst homologous or paralogous reference DNA sequences present in different organisms or members of a population, represents the outcome of an experiment that can be informative for predicting whether a given mutation or allele variation in a prospective parent's genome is likely to be deleterious to their child.

This experiment is the process of evolution, which has governed the replication and diversification of life on Earth. Today, there are many species, and individuals within a species all contain copies of genetic material which is derived from common ancestral versions. As species and individuals reproduce and copy their DNA, mutations appear which make these descendent copies distinct from the parental versions. The eventual fate of such new mutations, whether they will continue to be passed along to offspring or eventually die out, is determined by a stochastic process that is influenced by the mutation's effect on the reproductive fitness of the organism. Mutations that have no functional effect (neutral mutations) or are beneficial to an organism (positive mutations) are more likely to eventually increase in frequency and persist in the population, increasing diversity or replacing their parental version. In contrast, mutations which lower the reproductive fitness of an organism (negative or deleterious mutations) are unlikely to persist and contribute to future genetic variation.

Over the course of evolutionary time, a great many mutations have appeared and persisted, leading to the present diversity amongst DNA sequences derived from a common ancestor. However, this diversity is not equally distributed amongst all sequence positions in a genome. Although mutations are essentially introduced during the replication process independent of any functional effect they may have, the evolutionary filtering process is greatly influenced by such effects. As such, when comparing the genomes of several species or individuals today, we see that some areas are conserved (such as having the same coding sequence and/or non-coding sequence), while others have much more greatly diverged (having very diverged sequences from each other or relative to the ancestral copy number).

Reference is made to FIG. 1, which shows an example of an alignment of multiple genetic sequences (SEQ ID Nos.: 1-36, proceeding from top to bottom, respectively) according to an embodiment of the invention. In the example of FIG. 1, the multiple aligned reference genetic sequences represent a portion of the DNA sequence coding for the PEX10 proteins present in organisms from multiple vertebrate species. Item A in the figure shows a nucleic acid genetic locus which is completely conserved across all species in the alignment, as all species have a Guanine (symbolized by the letter G) at this locus position. Although many mutations that change the amino acid at this position have undoubtedly been introduced into this gene over the course of the 500 million years of vertebrate evolution, the fact that no such mutation persists today is a strong indication that such mutations are likely to be deleterious and reduce evolutionary fitness. In contrast, the position in the gene indicated by item B in FIG. 1 is much more variable, with different species having at that locus position one of the following DNA bases: Guanine (G), Adenine (A), Thymine (T), Cytosine (C). The diversity of DNA (or alternatively the amino acids encoded by the DNA) at this genetic locus provides an indication that it is relatively less likely that a mutation at this position in a parents genotype will be deleterious, relative to a mutation at the genetic locus position indicated by item A.

Assessing the Likelihood in Deleterious Alleles Based Directly on a Multiple Sequence Alignment A multiple sequence alignment of present day reference genetic sequences may be derived from common ancestral genetic loci of multiple species (e.g. different vertebrate sequenced genomes) or multiple individuals within a single species (e.g. a collection of human sequences). A substantially large sample size of organisms, populations or species (e.g., tens, hundreds, or more) may be used for statistically significant likelihoods, for example, to reduce bias error due to a skewed sample set.

Embodiments of the invention may compute a measure of evolutionary variation of alleles f at each of one or more aligned genetic loci as a function of variation in alleles F at corresponding aligned genetic loci in the multiple sequence alignment (MSA). The measure of evolutionary variation of alleles f may be transformed into a likelihood or score s associated with a relative propensity that this allele mutation would be damaging if produced in a child. This likelihood or score s may be derived, for example, using two functional transformations F and S, to convert columns of aligned genetic loci of a multiple sequence alignment (MSA) and a putative mutation or allele in a virtual progeny into a propensity score or likelihood s relevant to assessing the effect of that particular allele or mutation on the virtual progeny, for example, as shown in equation (1):

$$\text{Multiple Sequence Alignment (MSA)} \rightarrow f = F(\text{MSA}) \rightarrow s = S(f) \quad (1)$$

The first functional transformation shown in equation (1), f=F(MSA), is used to compute a measure of evolutionary variation of alleles f at each of one or more genetic loci derived from one or more common ancestral genetic loci in the multiple organisms as a function of variation in alleles F at corresponding aligned genetic loci in the multiple aligned genetic sequences. The first functional transformation may create a raw score that quantifies the relative amount of sequence conservation at the one or more genetic loci. There are many possible instantiations of this function that may be used according to embodiments of the invention. For example, one such function may input information from the DNA or amino acid genetic sequences present in the alignment and output a Shannon entropy of the sequence characters at each of the one or more genetic loci. Denoting a frequency of a particular symbol (DNA base or amino acid) at a particular genetic locus or column position, (j), in a multiple sequence alignment as $P_i$, i={A, C, G, T} (for DNA, or the set of amino acid symbols if considering a protein alignment), the Shannon entropy function may be calculated, for example, as shown in equation (2):

$$F(\text{MSA}_j) = \Sigma_i p_i \cdot \log_2 p_i \quad (2)$$

Another example of the first functional transformation shown in equation (1), f=F(MSA), may take the average pairwise difference between different symbols (S) in an aligned sequence column of length N, for example, as in equation (3):

$$F(\text{MSA}_j) = \binom{N}{2}^{-1} \sum_{i=1}^{N} \sum_{k=(i+1)}^{N} \begin{Bmatrix} 1 & \text{if } S_i \neq S_k \\ 0 & \text{if } S_i = S_k \end{Bmatrix} \quad (3)$$

Other possible functional forms of the first functional transformation, F(MSA), may calculate a distance metric from a particular species or sequence in the reference alignment. For example, the function may rank all the sequences in the alignment according to their Hamming distance from the reference (e.g., human) sequence, and then calculate the rank of the first sequence with a divergent symbol at the relevant position in the alignment, or if ranking a particular mutation, the rank of the first sequence matching that particular mutation. Additional functional forms such as not using the ordinal rankings of sequences by Hamming distance, but instead using the Hamming distance itself as the metric may be used.

Additionally, the function F(MSA) need not return a single value or be a function of a single column in the multiple sequence alignment. The function may be a composite function of one or more of the functions previously described in addition to others (e.g., $F_1$, $F_2$, $F_3$, . . . ), and may output a vector of values (e.g., ($s_1$, $s_2$, $s_3$, . . . )) rather than a single value. The function may also take as input multiple columns (j), or even the entire alignment, when calculating the value(s), f, and may also take as input a particular mutation under consideration, which may or may not affect the calculation of the values returned by the function.

The second functional transformation specified by equation (1), s=S(f), is a function which converts the measure of evolutionary variation of alleles into a relative propensity or likelihood of being damaging. Many possible instantiations of this function are also possible. For example, a function s=S(f) may score the value(s) of f according to its ranking in the empirical distribution of values for all mutations or alleles considered, or that could be considered, based on a collection of multiple reference sequence alignments. Other scoring methods may also be used. For example, a function trained to discriminate mutations in a database of known or suspected to be damaging alleles from neutral alleles may be used to assess the likelihood of damage (e.g., using any variety of statistical models or derived variants from experimental findings), or a function which is trained to assess the likelihood of a mutation reaching a certain frequency in the population. In all cases, this functional transformation, in combination with the first, allows particular genetic allele mutations to be ranked and assessed for likelihood of survival or damage if produced in a child.

Creating Functional Forms of the Measure of Evolutionary Variation F(MSA) Using Phylogenetic History for Assessing Likelihoods of Deleterious Effects of Alleles Embodiments of the invention may model the phylogenetic history of the multiple reference aligned genetic sequences (MSA) for the purpose of assessing the likelihood of damaging effects of an allele mutation in a new organism.

Because DNA replication is semi-conservative, the evolutionary history of a DNA molecule may be represented by a bifurcating tree, known as a "phylogenetic" tree, that represents the known or inferred historical or evolutionary relationships between present day extant reference genetic sequences. A large body of scientific literature has developed over the past 30 years that studies the problem of inferring this tree from present day sequences. Typically, such models envision the evolutionary process between nodes of the tree as being similar to a general time reversible (GTR) Markov chain. In these models, in an interval of time, t, there is a certain probability that a base in the sequence will mutate, or transition to another base (e.g., A→C). Such models may be described using a transition matrix that describes the relative probability of transition from one base to another, for example, as shown in equation (4):

$$Q = \begin{array}{c} \\ T \\ C \\ A \\ G \end{array} \begin{array}{c} \begin{matrix} T & C & A & G \end{matrix} \\ \begin{pmatrix} \bullet & a\pi_C & b\pi_A & c\pi_G \\ a\pi_T & \bullet & d\pi_A & e\pi_G \\ b\pi_T & d\pi_C & \bullet & f\pi_G \\ c\pi_T & e\pi_C & f\pi_A & \bullet \end{pmatrix} \end{array} \quad (4)$$

In equation (4) above, the elements of the transition matrix Q define a probability that each base denoted by the row will transition to each base denoted by the column, for example, in an infinitely small evolutionary time interval Δt. Note that the diagonal terms in the transition matrix are not shown, as they are simply equal to one minus the other elements in the row (the probabilities of the elements in each row sum to 1). The $\pi_i$ terms represent the equilibrium frequency of the nucleotide bases {i=A, C, G, T}, and the symbols a, b, c, d, e and f are parameters that further govern the substitution dynamics. This matrix represents a generalized time-reversible model, in which each rate below the diagonal equals a reciprocal rate above the diagonal multiplied by the equilibrium ratio of the two bases. Equation (4) is only one example of a substitution matrix used for phylogenetic inference.

Reference is made to FIG. 2, which schematically illustrates an example of a phylogenetic tree inferred from a multiple sequence alignment, for example, as shown in FIG. 1, according to an embodiment of the invention. The length of the branches shown in the tree may represent or be a function of an inferred number of substitutions or allele mutations per genetic locus that have occurred from its direct ancestral sequence. In the example shown in FIG. 2, a scale bar for the branch lengths is shown for a 0.2 branch length. The phylogenetic tree may be directly inferred using the Markov model described above. In inferring the tree, the likelihood of a tree and its branch length (e.g., given in units of expected substitutions) are maximized by varying the tree or branch lengths, until a tree with the highest likelihood is found. Alternatively, a prior probability distribution, as used in Bayesian statics, may be specified for all parameters in the phylogenetic model, and several trees may be sampled according to their posterior probability distribution, as used in Bayesian statics.

After fitting the Markov model that accounts for the phylogenetic history of the sequence alignment, whether using a Bayesian approach or maximum likelihood approach, embodiments of the invention may provide not only an inferred phylogenetic tree, but also a model for the evolutionary process of the multiple reference sequences in that tree.

Embodiments of the invention may use this evolutionary model to directly assess the likelihood that a mutation is damaging by examining the probability that a mutation found in a parent's genome persists into the future. That is, rather than using the model to infer the past history of evolution, the model is trained using the outcomes of the past and then used to calculate the likelihood of an allele persisting into the future. Because this likelihood is directly related to the probability that the allele is damaging (less likely mutations being more likely to be damaging), this phylogenetic approach, which directly accounts for the past history of the sequence in a parametric model, is a uniquely valuable functional form for the F(MSA) specified by equation (1).

Important extensions to the phylogenetic model are those which either change the model to account for sequence context (e.g., information about sequence location or what a sequence encodes, such as, methylation or homopolymer status) and functional effect (e.g., synonymous vs. non-synonymous, or affecting or not affecting expression), or that partition the sequence in some way to account for varying rates of substitutions, for example, based on the location of loci in the genome.

To account for varying rates of substitutions, for example, instead of the direct application of the substitution rate matrix in equation (4) to all sequence substitutions, an alternate model may specify that although the relative rates of different types of substitutions at all alignment positions was governed by (4), the global rate at each site (that is the total mutation rate, denoted $\mu$), may vary across sites or loci in the genome. A multitude of such models are possible. For example, the rates at different genetic loci may be drawn from a parametric distribution, such as a F-distribution that is also fit during the modeling procedure, or the distribution of rates may be derived from several categories of possible distributions. In one embodiment, this model may specify two different distribution categories (such as, conserved or rapidly evolving categories) and then train the model to identify to which distribution category the observed sequence belongs, for example, using a hidden Markov procedure. In some embodiments of the invention, the inferred or posterior probability that a genetic locus or mutation belongs to a category in the phylogenetic model may be returned by the F(MSA) function instead of the likelihood itself.

To account for functional effects, the phylogenetic model used to form the likelihood for the F(MSA) function may directly account for the functional consequence of a mutation. For example, the coding sequence of a protein is determined by triplets of neighboring DNA nucleotides that form a functional unit referred to as a "codon." A mutation in a nucleotide within a codon may either have a functional effect of changing the amino acid sequence encoded by that codon (in which case it is referred to as "non-synonymous" since the mutation encodes for a different amino acid sequence) or may be a substitution with no functional effect on the amino acid encoded due to the redundancy of the genetic code (in which case it is referred to as "synonymous" since the mutation encodes for the same amino acid sequence). The Markov model that may be used in predicting the likely damaging effect of a mutation may directly account for such functional effects. For example, the transition probability of mutating from nucleotide i to j specified by the ijth matrix Q element $q_{ij}$ in equation (4), may be replaced by an instantaneous transition probability $t_{ij}$, for example, defined by equation (5).

$$t_{ij} = \begin{cases} \omega q_{ij} & \text{if } i \to j \text{ is non-synonymous} \\ q_{ij} & \text{if } i \to j \text{ is synonymous} \end{cases} \quad (5)$$

This would allow a new instantaneous transition matrix, T, to be used in the model, and a new parameter, $\omega$, which is equal to the non-synonymous to synonymous substitution rate to be used in predicting the likelihood that an allele is damaging or that it persists into the future. In practice, the $\omega$ parameter may be constant for an entire multiple sequence alignment, may be assigned to each codon position in the alignment by assuming they are drawn from some hierarchical distribution, or may be uniquely assigned to each codon position. The substitution model specified by equation (5) may also be altered to account for each combination of the 64×64 possible elements of a transition matrix representing the rate in which each of the 64 possible codons (e.g., the $4^3=64$ different combinations of four nucleotide states (A, T, C, G) at three nucleotide positions in each codon) transition to each of the 64 possible codons. In all instantiations of the evolutionary model, the functional effect of a sequence change, whether on the amino acid, regulatory context or other biological context may be directly accounted for, and used to predict the likelihood that the allele was damaging.

Figure 3:
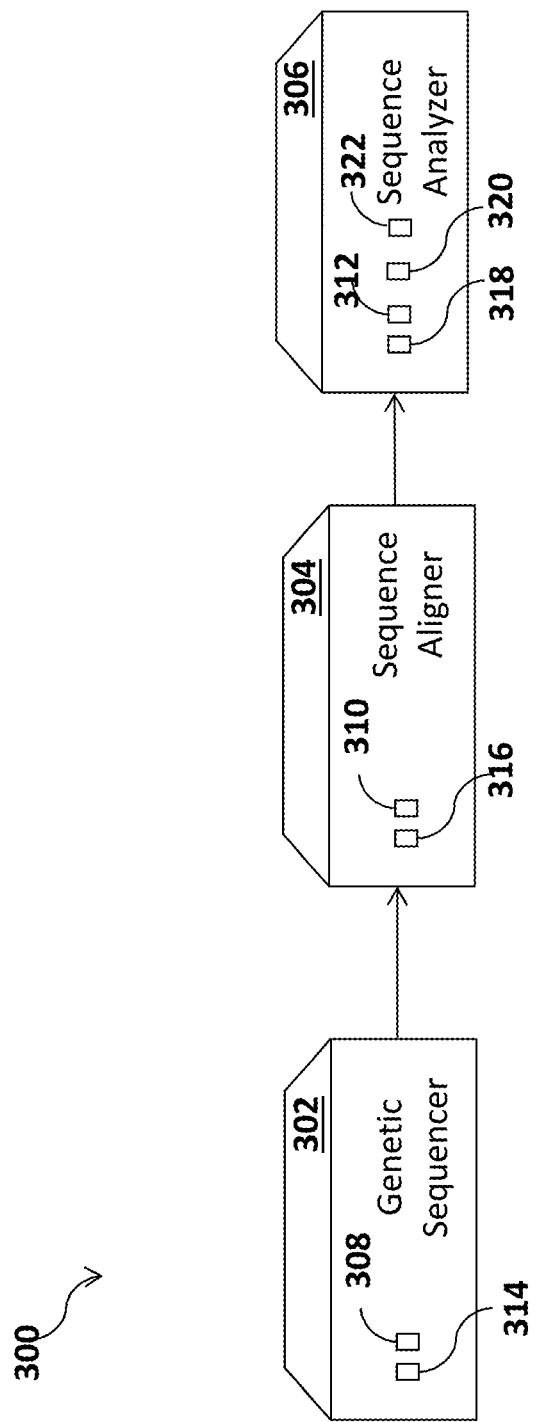
FIG. 3 schematically illustrates a system for executing one or more methods according to embodiments of the invention.

Reference is made to FIG. 3, which schematically illustrates a system 300 according to an embodiment of the invention.

System 300 may include a genetic sequencer 302, a sequence aligner 304 and/or a sequence analyzer 306. Units 302-306 may be implemented in one or more computerized devices as hardware or software units, for example, specifying instructions configured to be executed by a processor. One or more of units 302-306 may be implemented as separate devices or combined as an integrated device.

Genetic sequencer 302 may input biological samples, such as, blood, tissue, or saliva, or information derived therefrom, of each real (living) potential parent and may output the potential parent's genetic sequence including the individual's genetic information at one or more genetic loci, for example, a human genome.

Figure 4:
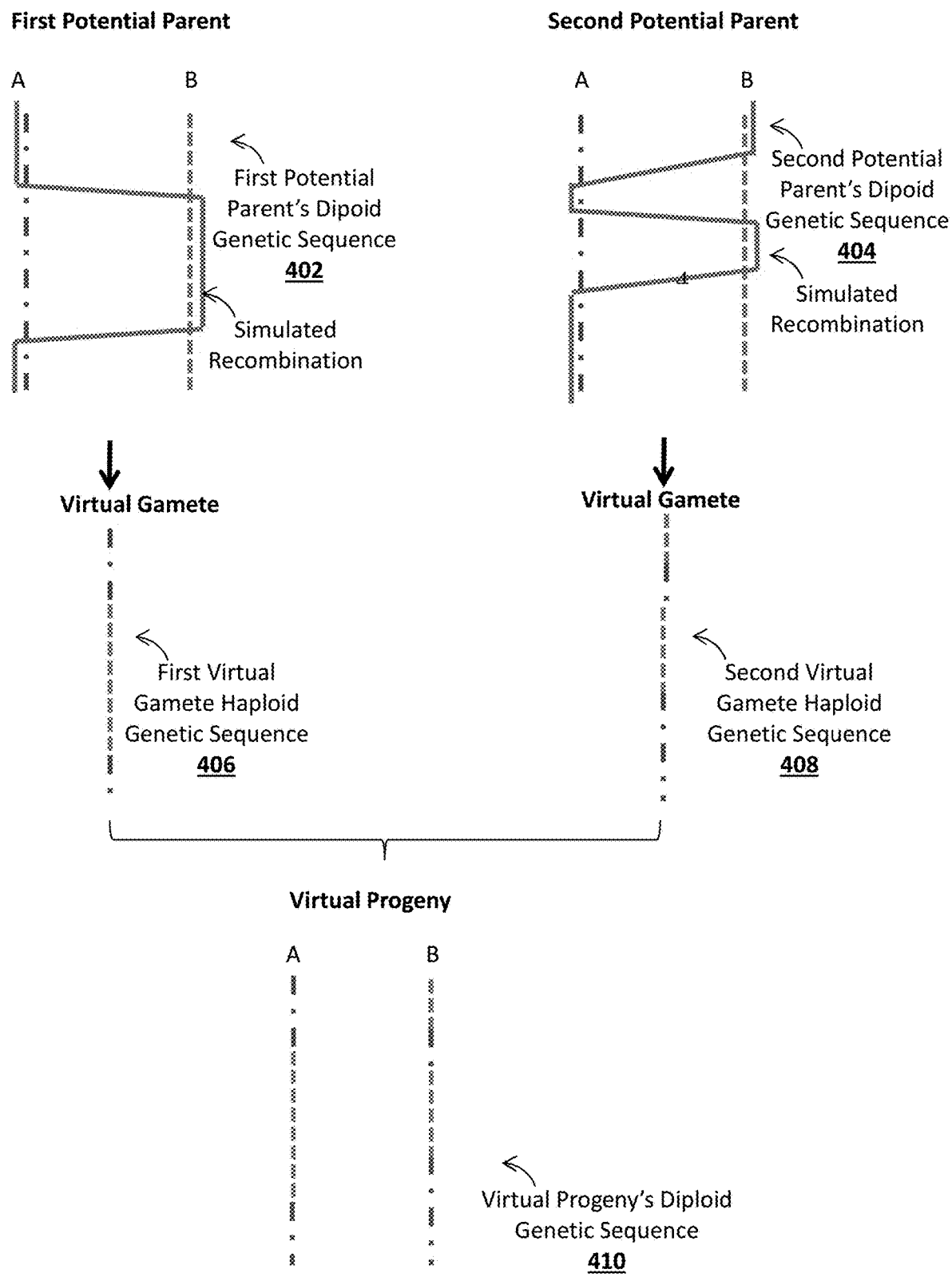
FIG. 4 schematically illustrates an example of simulating a hypothetical mating of two potential parents for generating a virtual progeny according to an embodiment of the invention.

Sequence analyzer 306 may input two potential parent's genetic sequences to simulate a mating by combining genetic information therefrom and output a virtual progeny genetic sequence of a virtual gamete, for example, as described in reference to FIG. 4.

Sequence aligner 304 may align one or more loci of the virtual progeny genetic sequence and a plurality of reference genetic sequences of extant organisms from one or more species.

Sequence analyzer 306 may input the multiple sequence alignment and may compute a measure f of evolutionary variation of alleles at one or more genetic loci, which may be transformed into one or more likelihoods or scores s associated with a relative propensity that these alleles would be damaging if produced in a child.

Genetic sequencer 302, sequence aligner 304, and sequence analyzer 306 may include one or more controller(s) or processor(s) 308, 310, and 312, respectively, configured for executing operations and one or more memory unit(s) 314, 316, and 318, respectively, configured for storing data such as genetic information or sequences and/or instructions (e.g., software) executable by a processor, for example for carrying out methods as disclosed herein. Processor(s) 308, 310, and 312 may include, for example, a central processing unit (CPU), a digital signal processor (DSP), a microprocessor, a controller, a chip, a microchip, an integrated circuit (IC), or any other suitable multi-purpose or specific processor or controller. Processor(s) 308, 310, and 312 may individually or collectively be configured to carry out embodiments of a method according to the present invention by for example executing software or code. Memory unit(s) 314, 316, and 318 may include, for example, a random access memory (RAM), a dynamic RAM (DRAM), a flash memory, a volatile memory, a non-volatile memory, a cache memory, a buffer, a short term memory unit, a long term memory unit, or other suitable memory units or storage units. Genetic sequencer 302, sequence aligner 304, and sequence analyzer 306 may include one or more input/output devices, such as output display 320 (e.g., such as a monitor or screen) for displaying to users results provided by sequence analyzer 306 and an input device 322 (e.g., such as a mouse, keyboard or touchscreen) for example to control the operations of system 300 and/or provide user input or feedback, such as, selecting one or more models or phylogenetic trees, selecting one or more genus or species to use for generating the models, selecting input genetic sequences, selecting two potential parents or multiple donor candidates from a pool of potential parents with which to simulate mating, selecting a number of iterations for simulating a mating with a different pair of virtual gametes in each iteration from each pair of potential parents, etc.

Reference is made to FIG. 4, which schematically illustrates an example of simulating a hypothetical mating of two (i.e. a first and a second) potential parents for generating a virtual progeny according to an embodiment of the invention.

For each of the two potential parents, a processor (e.g., sequence analyzer processor 312 of FIG. 3) may receive a potential parent's diploid genetic sequence 402, 404. A "diploid" genetic sequence includes two alleles from the two sets of chromosomes respectively labeled "A" and "B" at each genetic locus of a diploid cell of the potential parent, whereas a "haploid" genetic sequence includes one allele from one chromosome at each genetic locus of a haploid cell of the potential parent. For each of the two potential parents' diploid genetic sequences 402 and 404, the processor may simulate genetic recombination of the two sets of chromosomes A and B from the parent's diploid genetic sequence 402, 404 (having two alleles at each genetic locus) to generate a virtual gamete haploid genetic sequence 406, 408 (having one allele per genetic locus). The processor may simulate recombination by progressing locus-by-locus along a "haplopath" through each parent's diploid genetic sequence 402, 404 and selecting one of the two alleles at each genetic locus (either the allele in chromosome A or the allele in chromosome B). The selection of alleles may be at least partially random and/or at least partially non-random, for example, based on defined correlations between alleles at different loci referred to as "linkage disequilibrium". The haploid genetic sequence may mimic or simulate recombination of the genetic material in the two chromosomes A and B to form a discrete haploid genetic sequence of a virtual gamete 406, 408, e.g., a virtual sperm or virtual egg.

The two virtual gamete haploid genetic sequences 406 and 408 for the two respective potential parents may be combined to simulate a mating between the first and second potential parents resulting in a virtual progeny diploid genetic sequence 410 (a discrete genome of a child potentially to be conceived).

Since the selection of alleles is at least partially random, this mating is just one of the many possible genetic combinations for the first and second potential parents. This process may be repeated multiple times (e.g., hundreds or thousands of times), each time following a different recombination path (e.g., a different sequence of alleles selected) for one or both of the potential parents, to generate multiple genetic permutations that are possible for mating the first and second potential parents. The virtual progeny diploid genetic sequence 410 may include a single (e.g., most probable) genetic sequence or a probability distribution of multiple possible sequences, for example, to indicate, for many possible matings, the overall likelihood of each of multiple alleles at each of one or more loci in a virtual or hypothetical progeny.

Embodiments of the invention may use methods for simulating a mating between two potential parents and generating a virtual progeny genetic sequence described in U.S. Pat. No. 8,805,620, which is incorporated herein by reference in its entirety. Other methods may also be used.

Once the virtual progeny genetic sequence 410 is generated, it may be aligned with one or more reference genetic sequences of one or more organisms in a multiple sequence alignment (MSA). Based on a measure of variation between organisms at the aligned genetic loci, the virtual progeny may be assigned one or more of the likelihoods that one or more alleles or mutations in the virtual genetic sequence 410 would be deleterious, for example, if replicated in a real living progeny.

Figure 5:
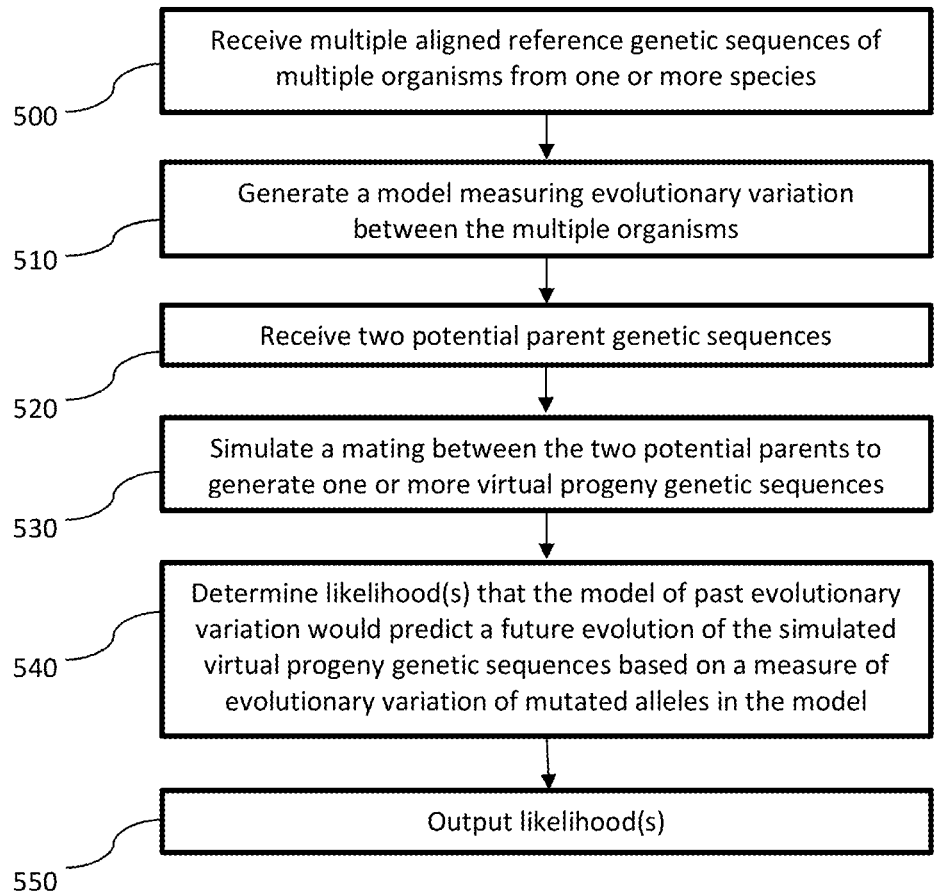
FIG. 5 is flowchart of a method for using the evolution of multiple organisms to predict deleterious mutations in virtual progeny according to an embodiment of the invention.

Reference is made to FIG. 5, which is a flowchart of a method for using the past evolution of multiple organisms to predict deleterious mutations in future virtual, hypothetical or simulated (non-living) potential progeny, in accordance with an embodiment of the invention.

In operation 500, a processor (e.g., sequence analyzer processor 312 of FIG. 3) may receive multiple aligned reference genetic sequences of multiple extant organisms representative of one or more species or populations (e.g., as shown in FIG. 1). The reference genetic sequences may be sequenced by a genetic sequencer (e.g., sequencer 302 of FIG. 3) or pre-stored and retrieved from a memory or database (e.g., one or more of memory unit(s) 314 and/or 318) and may be aligned by a sequence aligner (e.g., sequence aligner 304 of FIG. 3) or pre-aligned in the memory or database.

In operation 510, the processor may build or obtain a model representing measures of evolutionary variation of alleles or nucleotides at one or more aligned genetic loci between the multiple organisms. The model may be a single-species model (e.g., the multiple organisms are from the same single species) or a multi-species model (e.g., the multiple organisms are from different multiple species). The model may include, for example, a phylogenetic tree (e.g., as shown in FIG. 2), or another data structure.

In operation 520, the processor may receive genetic sequences of two potential parents (e.g., potential parent genetic sequences 402 and 404 of FIG. 4). The sequences may be derived by a sequencer (e.g., genetic sequencer processor 308 of FIG. 3) from biological samples, such as, blood, saliva, etc., of the two potential parents. The two potential parents may include two individuals interested in mating together, or one individual interested in conceiving a child and another individual from a group of genetic donors. The biological samples for different potential parents may be obtained and sequenced at the same or different times and may be stored for later analysis.

In operation 530, the processor may simulate a mating between the two potential parents by combining their genetic sequences to generate one or more virtual progeny genetic sequences (e.g., sequence 410 of FIG. 4). The processor may generate a virtual gamete (haploid genetic sequence) for each potential parent by at least partially randomly selecting one of two allele copies in the parent's two chromosomes (diploid genetic sequence) to simulate recombination at each of a sequence of genetic loci. A virtual gamete for each of the two potential parents (e.g., one virtual sperm and one virtual egg) may be combined to generate the genetic sequence of the virtual progeny. Multiple virtual gametes may be generated for each potential parent by repeating the recombination process each time selecting a different at least partially random sequence of alleles. Multiple virtual progeny genetic sequences may be generated for multiple pairs of potential parents by repeating the step of combining two virtual gametes for each of a plurality of different combinations of two virtual gametes. In one embodiment, the independent carrier status of an individual may be determined by simulating a mating combining the individual's genetic sequence information with that of a sample, averaged, or reference genetic sequence of the same species.

In operation 540, the processor may use the model of operation 500 defining the evolutionary past variation among multiple extant organisms of different populations or species to predict or interpolate a likelihood or probability of evolutionary health of the virtual progeny simulated in operation 530. The processor may determine the differences between the virtual progeny genetic sequence and one or more aligned reference genetic sequences and may assign each allele (or only different or mutated alleles) a measure of evolutionary variation that is a function of variations in alleles at corresponding aligned genetic loci in the multiple aligned genetic sequences (e.g., loci derived from one or more common ancestral genetic loci in the multiple organisms). The processor may compute one or more likelihoods that an allele mutation at each of the one or more genetic loci in the simulated virtual progeny will be deleterious based on the measure of evolutionary variation of alleles at the corresponding aligned genetic loci for the multiple organisms. The likelihoods may include one or more likelihoods or likelihood distributions for one or more alleles, one or more allele mutations, one or more genes, one or more codons, one or more genetic loci or loci segments, for one or more virtual progeny of two potential parents (e.g., generated by repeatedly simulating a mating using different virtual gamete(s) in each iteration) and/or for one or more pairs of potential parents (e.g., generated by repeatedly simulating a mating step, in each iteration using the genetic information of the same first one of the two potential parents and a different second one of the two potential parents iteratively selected from a plurality of genetic donor candidates). The one or more likelihoods may be compared to one or more thresholds or other statistical models to predict if (or a likelihood or degree in which) an allele mutation will be deleterious in the virtual progeny. For example, mutations at genetic loci with relatively constant or fixed alleles and relatively lower measures of evolutionary variation may be associated with relatively higher likelihoods of deleterious traits, whereas mutations at genetic loci with relatively volatile or changing alleles and relatively higher measures of evolutionary variation may be associated with relatively lower likelihoods of resulting in deleterious traits.

In operation 550, an output device (e.g., output device 320 of FIG. 3) may output or display, e.g., to a user, the one or more likelihoods or likelihood distributions that a hypothetical child conceived by the two potential parents having the virtual progeny genetic sequence generated in operation 530 would have deleterious traits, or other data generated in operation 540. For example, the output device may output one or more likelihoods that an allele mutation at each of the one or more genetic loci in the simulated virtual progeny will be deleterious based on the measure of evolutionary variation of alleles at the corresponding aligned genetic loci for the multiple organisms.

Other or different operations or orders of operations may be used and operations may be repeated, e.g., until the likelihoods converge or asymptotically approach a statistically stable result.

In accordance with embodiments of the present invention and as used herein, the following terms are defined with the following meanings, unless explicitly stated otherwise.

As used herein, "haploid cell" refers to a cell with a single set (n) of unpaired chromosomes.

"Gametes", as used herein, are specialized haploid cells (e.g., spermatozoa and oocytes) produced through the process of meiosis and involved in sexual reproduction.

As used herein, "diploid cell" has a homologous pair of each of its autosomal chromosomes, and has two copies (2n) of each autosomal genetic locus.

The term "chromosome", as used herein, refers to a molecule of DNA with a sequence of base pairs that corresponds closely to a defined chromosome reference sequence of the organism in question.

The term "gene", as used herein, refers to a DNA sequence in a chromosome that codes for a product (either RNA or its translation product, a polypeptide) or otherwise plays a role in the expression of said product. A gene contains a DNA sequence with biological function. The biological function may be contained within the structure of the RNA product or a coding region for a polypeptide. The coding region includes a plurality of coding segments ("exons") and intervening non-coding sequences ("introns") between individual coding segments and non-coding regions preceding and following the first and last coding regions respectively.

As used herein, "locus" refers to any segment of DNA sequence defined by chromosomal coordinates in a reference genome known to the art, irrespective of biological function. A DNA locus may contain multiple genes or no genes; it may be a single base pair or millions of base pairs.

As used herein, an "allele" is one of two or more existing genetic variants of a specific polymorphic genomic locus.

As used herein, "genotype" refers to the diploid combination of alleles at a given genetic locus, or set of related loci, in a given cell or organism. A homozygous subject carries two copies of the same allele and a heterozygous subject carries two distinct alleles. In the simplest case of a locus with two alleles "A" and "a", three genotypes may be formed: A/A, A/a, and a/a.

As used herein, "genotyping" refers to any experimental, computational, or observational protocol for distinguishing an individual's genotype at one or more well-defined loci.

As used herein, "linkage disequilibrium" is the non-random association of alleles at two or more loci within a particular population. Linkage disequilibrium is measured as a departure from the null hypothesis of linkage equilibrium, where each allele at one locus associates randomly with each allele at a second locus in a population of individual genomes.

As used herein, a "genome" is the total genetic information carried by an individual organism or cell, represented by the complete DNA sequences of its chromosomes.

As used herein, a genetic "trait" is a distinguishing attribute of an individual, whose expression is fully or partially influenced by an individual's genetic constitution.

As used herein, "disease" refers to a trait that is at least partially heritable and causes a reduction in the quality of life of an individual person.

As used herein, a "phenotype" includes alternative traits which may be discrete or continuous. Phenotypes may include both traits and diseases.

As used herein, a "haplopath" is a haploid path laid out along a defined region of a diploid genome by a single iteration of a Monte Carlo simulation or a single chain generated through a Markov process. A haplopath is generated through the application of formal rules of genetics that describe the reduction of the diploid genome into haploid genomes through the natural process of meiosis. It may be formed by starting at one end of a personal chromosome or genome and walking from locus to locus, choosing a single allele at each step based on available linkage disequilibrium information, inter-locus allele association coefficients, and formal rules of genetics that describe the natural process of gamete production in a sexually reproducing organism.

A "virtual gamete" is a data structure representing an imaginary non-existing gamete, for example, simulated by at least partially randomly selecting genetic information from both chromosomes of a single potential parent genetic sequence. A virtual gamete may represent information selected along a single haplopath that extends across one or more loci, such as, an entire genome.

As used herein, a "virtual progeny genetic sequence" is a data structure representing the genetic information of an imaginary non-existing virtual progeny. The virtual progeny genetic sequence is, for example, a discrete genetic combination of two virtual gametes.

As used herein, a "variant" is a particular allele at a locus where at least two alleles have been identified.

As used herein, a "mutation" has the same meaning as a "mutant allele" which is a variant that causes a gene to function abnormally.

Embodiments of the invention may include an article such as a computer or processor readable non-transitory storage medium, such as for example a memory, a disk drive, or a USB flash memory device encoding, including or storing instructions, e.g., computer-executable instructions, which when executed by a processor or controller, cause the processor or controller to carry out methods disclosed herein.

Different embodiments are disclosed herein. Features of certain embodiments may be combined with features of other embodiments; thus certain embodiments may be combinations of features of multiple embodiments.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A computer-implemented method for predicting variants being deleterious in virtual progenies, a deleterious variant associated with disease or reduced likelihood of surviving or reproducing, the method comprising:
   retrieving, from a computer memory, multiple aligned genetic sequences representing genetic material obtained from DNA samples of multiple organisms of one or more different species, the aligned genetic sequences aligning genetic sequences of the multiple organisms at one or more genetic loci;
   generating a plurality of virtual progenies of two potential parents by combining at least a portion of genetic information representing genetic material obtained from biological samples of the two potential parents, the generating of the virtual progenies comprising:
   (i) retrieving, for each parent, a diploid genetic sequence comprising two alleles at each genetic locus,
   (ii) selecting, for each parent, one of the two alleles for each genetic locus, the selection progressing locus-by-locus along the diploid genetic sequence and based at least partially on a stochastic process,
   (iii) forming a haploid genetic sequence based on the selected alleles for each parent, the haploid genetic sequence representing a genetic sequence of a virtual gamete,
   (iv) combining the haploid genetic sequences of the two parents to form a virtual progeny diploid genetic sequence associated with a virtual progeny, and
   (v) repeating at least steps (ii) to (iv) multiple times to generate the plurality of virtual progenies of the two potential parents;
   aligning the plurality of virtual progenies with the multiple sequence alignment of the multiple organisms;
   retrieving a machine learning computer model that is trained based on at least the aligned genetic sequences of the multiple organisms, the machine learning computing model comprises a phylogenetic tree generated from the multiple aligned genetic sequences, the phylogenetic tree modeling evolutionary variations of allele variants, each evolutionary variation of an allele variant corresponding to a prediction of a likelihood that the allele variant would be deleterious;
   inputting aligned sequences of the plurality of virtual progenies to the machine learning computer model to compute one or more likelihoods that a particular allele variant in the plurality of virtual progenies will be deleterious based on the evolutionary variation of the particular allele variant of the plurality of virtual progenies aligned with the multiple sequence alignment of the multiple organisms, the one or more likelihoods computed based on a frequency with which the particular allele variant has occurred and persisted in the multiple organisms according to the phylogenetic tree.

2. The method of claim 1, wherein an additional virtual progeny is generated by combining genetic information of one of the two potential parents and a reference genetic information data set.

3. The method of claim 1, wherein the multiple organisms are from multiple different species.

4. The method of claim 1, wherein the multiple organisms are from a single species.

5. The method of claim 1, further comprising computing one or more functions of variation in alleles at corresponding aligned genetic loci between a genetic sequence of an individual organism and one or more reference genetic information data sets.

6. The method of claim 1, further comprising comparing the one or more likelihoods to one or more thresholds or other statistical models to predict if the particular allele variant is deleterious.

7. The method of claim 1, wherein the likelihood that the particular allele variant is deleterious is relatively higher for one or more variants at corresponding aligned genetic loci that have a relatively lower measure of evolutionary variations in alleles.

8. The method of claim 1, further comprising weighing the evolutionary variations at different genetic loci based on a distribution of mutation rates at the different genetic loci in the multiple aligned genetic sequences.

9. The method of claim 1, further comprising weighing the evolutionary variations at different genetic loci to identify genetic loci in which mutations have been observed in evolutionary history lower than a threshold rate.

10. The method of claim 1, wherein the phylogenetic tree is used to generate a function of variation in alleles that have proliferated in the multiple organisms over evolutionary history to predict likelihoods that such variations in alleles are deleterious.

11. The method of claim 10, wherein at least one of the likelihoods that one of such variations in alleles is deleterious is based on a frequency with which the one of such variations has occurred and persisted in the multiple organisms over evolutionary history.

12. The method of claim 10, wherein at least one of the likelihoods that one of such variations in alleles is deleterious is based on a proximity in the phylogenetic tree representing an evolutionary timescale between a reference genetic sequence of the same species as the two potential parents and one or more other species in which the one of such variations has occurred.

13. The method of claim 1, wherein the phylogenetic tree is defined by a model of probabilities that an allele i will mutate to an allele j over an interval of evolutionary time.

14. The method of claim 1, wherein at least one of the evolutionary variations of a second particular allele variant is a score that quantifies a relative amount of sequence conservation at an aligned genetic loci corresponding to the second particular allele variant.

15. The method of claim 1, wherein at least one of the evolutionary variations of a second particular allele variant based on a Shannon entropy of alleles at an aligned genetic loci corresponding to the second particular allele variant.

16. The method of claim 1, wherein at least one of the evolutionary variations of a second particular allele variant based on an average pairwise difference between different alleles at an aligned genetic loci corresponding to the second particular allele variant.

17. The method of claim 1, wherein at least one of the evolutionary variations is a composite of results of multiple functions for computing multiple measures of evolutionary variation for multiple genetic loci.

18. The method of claim 1, wherein at least one of the evolutionary variations corresponding to multiple different aligned genetic loci is derived from multiple common ancestral genetic loci.

19. The method of claim 1, wherein the one or more likelihoods are computed further based on training the machine learning computer model to discriminate between variants predefined to be deleterious and variants predefined not to be deleterious.

20. The method of claim 1, wherein the one or more likelihoods are computed further based on training the machine learning computer model to assess a likelihood of a variant reaching a certain frequency in a population.

21. The method of claim 1, wherein at least one of the evolutionary variations corresponding to one or more genetic loci is based on a ratio w of a non-synonymous substitution rate to a synonymous substitution rate, wherein a non-synonymous substitution is an allele substitution in a codon that does not change an amino acid encoded by the codon and a synonymous substitution is an allele substitution in the codon that does change the amino acid.

22. A system for executing a machine learning computer model to predict variants being deleterious in virtual progenies, a deleterious variant associated with disease or reduced likelihood of surviving or reproducing, the system comprising:
a memory configured to store multiple aligned genetic sequences representing genetic material obtained from DNA samples of multiple organisms of one or more different species; and
a processor configured to:
generate a plurality of virtual progenies of two potential parents by combining at least a portion of genetic information representing genetic material obtained from biological samples of the two potential parents, the generating of the virtual progenies comprising:
(i) retrieve, for each parent, a diploid genetic sequence comprising two alleles at each genetic locus,
(ii) select, for each parent, one of the two alleles for each genetic locus, the selection progressing locus-by-locus along the diploid genetic sequence and based at least partially on a stochastic process,
(iii) form a haploid genetic sequence based on the selected alleles for each parent, the haploid genetic sequence representing a genetic sequence of a virtual gamete,
(iv) combine the haploid genetic sequences of the two parents to form a virtual progeny diploid genetic sequence associated with a virtual progeny, and
(v) repeat at least steps (ii) to (iv) multiple times to generate the plurality of virtual progenies of the two potential parents;
align the plurality of virtual progenies with the multiple sequence alignment of the multiple organisms;
retrieve the machine learning computer model that is trained based on at least the aligned genetic sequences of the multiple organisms, the machine learning computing model comprises a phylogenetic tree generated from the multiple aligned genetic sequences, the phylogenetic tree modeling evolutionary variations of allele variants, each evolutionary variation of an allele variant corresponding to a prediction of a likelihood that the allele variant would be deleterious;
input aligned sequences of the plurality of virtual progenies to the machine learning computer model to compute one or more likelihoods that a particular allele variant in the plurality of virtual progenies will be deleterious based on the evolutionary variation of the particular allele variant of the plurality of virtual progenies aligned with the multiple sequence alignment of the multiple organisms, the one or more likelihoods computed based on a frequency with which the particular allele variant has occurred and persisted in the multiple organisms according to the phylogenetic tree.

23. The system of claim 22, wherein the processor is further configured to compute the one or more likelihoods based on a proximity in the phylogenetic tree representing an evolutionary timescale between a reference genetic sequence of the same species as the two potential parents and one or more other species in which the particular allele variant has occurred.

* * * * *